(12) United States Patent
Rojas et al.

(10) Patent No.: US 11,889,834 B2
(45) Date of Patent: Feb. 6, 2024

(54) BURKHOLDERIA CENOCEPACIA AND PSEUDOMONAS FLUORESCENS COMPOSITIONS AND METHODS OF USING THE SAME

(71) Applicant: THE BOARD OF TRUSTEES OF THE UNIVERSITY OF ARKANSAS, Little Rock, AR (US)

(72) Inventors: Clemencia M. Rojas, Fayetteville, AR (US); Ruben O. Morawicki, Fayetteville, AR (US); Ines Pinto, Fayetteville, AR (US); Alejandro Rojas, Springdale, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 16/561,697

(22) Filed: Sep. 5, 2019

(65) Prior Publication Data
US 2020/0068900 A1 Mar. 5, 2020

Related U.S. Application Data

(60) Provisional application No. 62/727,095, filed on Sep. 5, 2018.

(51) Int. Cl.
*A01N 63/00* (2020.01)
*C12N 1/20* (2006.01)

(52) U.S. Cl.
CPC .............. *A01N 63/00* (2013.01); *C12N 1/20* (2013.01)

(58) Field of Classification Search
None
See application file for complete search history.

(56) References Cited

U.S. PATENT DOCUMENTS 6,689,357 B2 * 2/2004 Casida, Jr. ............. C12N 1/205
424/93.47
2017/0233712 A1 * 8/2017 Shepherd ........... C12N 15/8281
800/279

FOREIGN PATENT DOCUMENTS

KR 100519469 * 10/2003
WO WO 2013130680 * 9/2013

OTHER PUBLICATIONS

Compant et al. Microbiol Rev (2008), vol. 32, pp. 607-626.*
Yasmin et al. PLoS ONE (2016).*
Akter, S., et al. (2016). In vitro evaluation of Pseudomonas bacterial isolates from rice phylloplane for biocontrol of Rhizoctonia solanil and plant growth promoting traits. J. Environ Biol. 37(4)567-602.
Arseneault, T., et al. (2016). Biocontrol of potato common scab is associated with High Pseudomonas fluorescens LBUM223 populations and phenazine-1-carboxylic acid biosynthetic transcript accumulation in the potato geocaulosphere. Phytopathology. 106(6):554-561.
Chandrasekaran, M., et al. (2016). Metaanalysis reveals that the genus Pseudomonas can be a better choice of biological control agent against bacterial wilt disease cause by Ralstonia solanacearum. Plant Pathol J. 32(3): 216-27.
Chin-A-Woeng TF, et al, 2000. Root colonization by phenazine-1-carboxamide-producing bacterium Pseudomonas chlororaphis PCL1391 is essential for biocontrol of tomato foot and root rot. Mol Plant Microbe Interact 13, 1340-5.
Cui, Z., et al. (2014). Susceptibility of the opportunistic Burkholderia glumae to copper surfaces following wet or dry surface contact. Molecules. J19(7):9975-85.
D'Aes J, et al., 2011. Biological control of Rhizoctonia root rot on bean by phenazine- and cyclic lipopeptide-producing Pseudomonas CMR12a. Phytopathology 101, 996-1004.
Degrassi G, et al, 2008. Identification, characterization and regulation of two secreted polygalacturonases of the emerging rice pathogen Burkholderia glumae. FEMS Microbiol Ecol 65, 251-62.
Devescovi G, et al., 2007. Involvement of a Quorum-Sensing-Regulated Lipase Secreted by a Clinical Isolate of Burkholderia glumae in Severe Disease Symptoms in Rice. Appl Environ Microbiol 73, 4950-8.
Dubouzet JG, et al., 2011. Screening for resistance against Pseudomonas syringae in rice-FOX *Arabidopsis* lines identified a putative receptor-like cytoplasmic kinase gene that confers resistance to major bacterial and fungal pathogens in *Arabidopsis* and rice. Plant Biotechnol J 9, 466-85.
Fuller, A. T., et al. (1971). Psudomonic acid: an antibiotic produced by Pseudomonas fluorescens. Nature. 234:416-417.
Glare T, et al., 2012. Have biopesticides come of age? Trends Biotechnol 30, 250-8.
Gomez-Lama Cabanas, C. et al. (2018). Indigenous *Pseudomonas* spp. Strains from the olive (*Olea europea* L) rhizosphere as effective biocontrol agents against Verticillium dahlia: from host roots to the bacterial genomes. Front. Microbiol. 2018. 9:277.
Haas D, et al, 2005. Biological control of soil-borne pathogens by fluorescent pseudomonads. Nat Rev Microbiol 3, 307-19.
Ham JH, et al, 2011. Burkholderia glumae: next major pathogen of rice? Molecular Plant Pathology 12, 329-39.
Howell CR, et al, 1979. Control of *Rhizoctonia solani* on cotton seedlings with Pseudomonas fluorescens and with an antibiotic produced by the bacterium. Phytopathology 69, 480-2.
Howell CR, et al, 1980. Suppression of Pythium ultimum-induced damping-off of cotton seedlings by Pseudomonas Tuorescens and its antibiotic, pyoluteorin. Phytopathology 70, 712-15.
Ilyama K, et al, 1995. A role of phytotoxin in virulence of Pseudomonas glumae Kurita et Tabeti. Japanese Journal Phytopath 61, 470-6.

(Continued)

*Primary Examiner* — Medina A Ibrahim
(74) *Attorney, Agent, or Firm* — QUARLES & BRADY LLP

(57) ABSTRACT

The present invention provides compositions comprising new strains of *Pseudomonas fluorescens* and *Burkholderia cenocepacia*. Secreted fraction compositions produced by these bacterial strains, and the methods for producing these compositions are also provided. Herein, the inventors demonstrate that these bacterial strains and compositions may be used to inhibit the growth of a broad spectrum of plant pathogens.

12 Claims, 10 Drawing Sheets

(56) References Cited

OTHER PUBLICATIONS

Figure 1C:
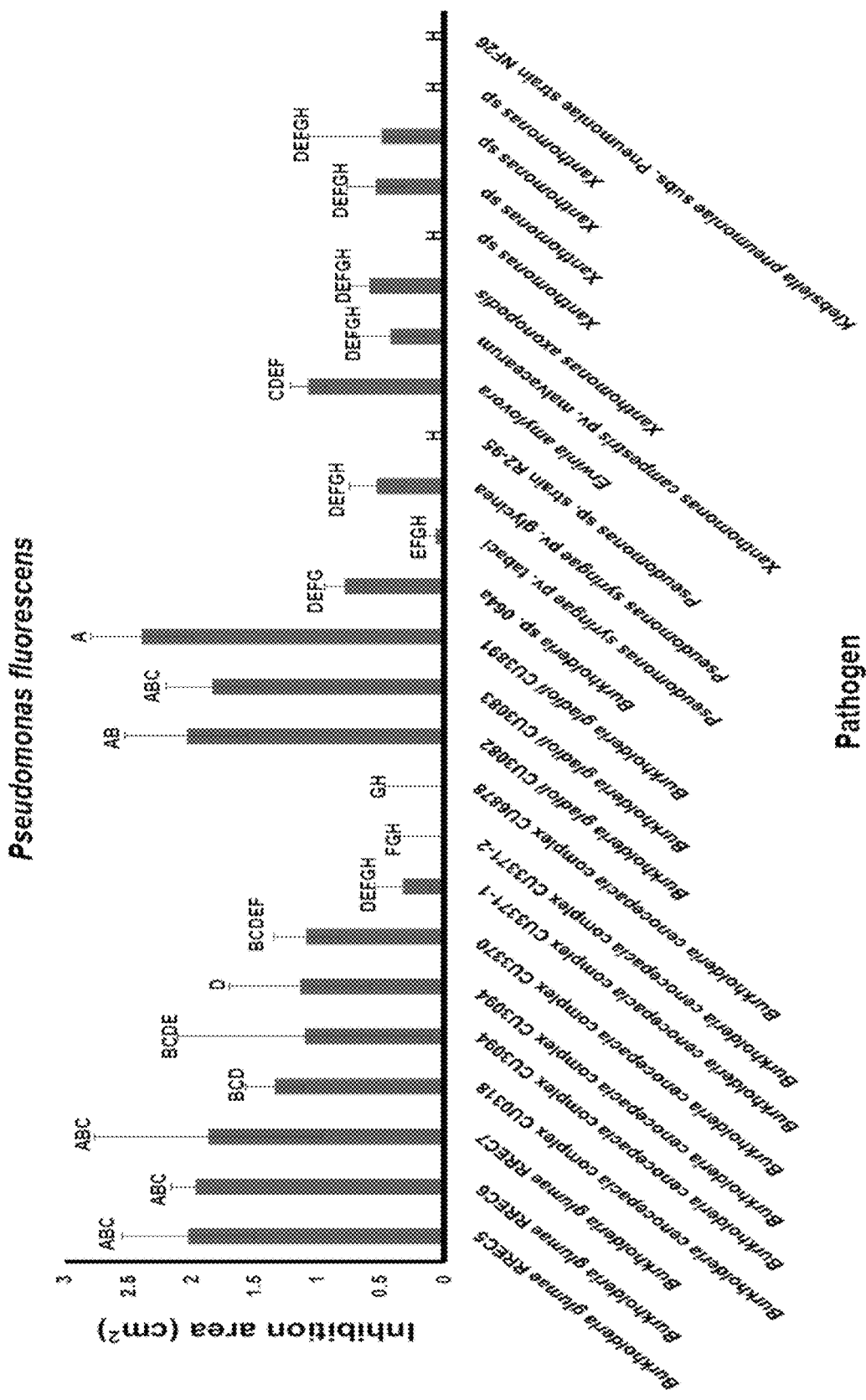

Jamali F, et al, 2009. Influence of host plant genotype, presence of a pathogen, and coinoculation with Pseudomonas Tuorescens strains on the rhizosphere expression of hydrogen cyanide- and 2,4-diacetylphloroglucinol biosynthetic genes in P. fluorescens biocontrol strain CHA0. Microb Ecol 57,267-75.
James, D. W., et al. (1986). Multiple antibiotics produced by Pseudomonas fluorescens HV37a and their differential regulation by glucose. Appl. Environ. Microbiol> 52 (5):1183-1189.
Kaur, R., et al. (2016). Evaluation of Pseudomonas fluorescens for the management of tomato early blight disease and fruit borer. J. Environ Biol. 37(5): 869-872.
Kawaradani M, et al, 2000. New selective medium for isolation of *Burkholderia glumae* from rice seeds. J. Gen. Plant Pathol 66, 234-7.
Keel C, et al., 1992. Suppression of root diseases by Pseudomonas fluorescens CHAO: importance of the bacterial secondary metabolite 2,4-diaceylphloroglucinol. Molecular Plant-Microbe Interactions 5, 4-13.
Kim J, et al., 2004. Quorum sensing and the LysR-type transcriptional activator ToxR regulate toxoflavin biosynthesis and transport in Burkholderia glumae. Mol Microbiol 54, 921-34.
Kloepper JW, et al, 1980. Pseudomonas siderophores: a mechanism explaining disease-suppressive soils. Current microbiology 4, 317-20.
Kohl J, et al, 2019. Mode of Action of Microbial Biological Control Agents Against Plant Diseases: Relevance Beyond Efficacy. Front Plant Sci 10, 845.
Lemanceau P, et al, 1992. Effect of pseudobactin 358 production by Pseudomonas putida WCS358 on suppression of fusarium wilt of carnations by nonpathogenic Fusarium oxysporum Fo47. Appl Environ Microbiol 58, 2978-82.
Maurhofer M, et al, 1994. Pyoluteorin production by Pseudomonas fluorescens strain CHA0 is involved in the suppression of Phythium damping-off of cress but not of cucumber. Eur J Med Chem Eur J Plant Pathol, 221-32.
Mazurier S, et al, 2009. Phenazine antibiotics produced by fluorescent pseudomonads contribute to natural soil suppressiveness to Fusarium wilt. ISME J 3, 977-91.
Milus EA, et al, 1997. Efficacy of Bacterial Seed Treatments for Controlling Pythium Root Rot of Winter Wheat. Plant Dis 81, 180-4.
Morrison, C.K., et al. (2017). Phenazine-1-carboxylic acid production by Pseudomonas fluorescens LBUM636 alters Phytophthora infestans growth and late blight development. Phytopathology. 107(3):273-279.

Mulaw, T, et al, 2018. Characterization and plant detection of bacteria that cause Bacterial Panicle Blight of rice. American Journal of Plant Sciences 9, 667-84.
Olorunleke, F.E., et al. 2015. Interplay between orfamides, sessilins and phenazines in the control of Rhizoctonia diseases by *Pseudomonas* sp. CMR12a. Environ Microbiol Rep 7:774-781.
Pieterse CM, et al, 2014. Induced systemic resistance by beneficial microbes. Annu Rev Phytopathol 52, 347-75.
Raaijmakers JM, et al, 2012. Diversity and natural functions of antibiotics produced by beneficial and plant pathogenic bacteria. Annu Rev Phytopathol 50, 403-24.
Shew AM, et al, 2019. Warming increases Bacterial Panicle Blight (Burkholderia glumae) occurrences and impacts on USA rice production. PLoS One 14, e0219199.
Shrestha, BK., et al. (2016). Biological Control Activities of Rice-Associated *Bacillus* sp. Strains against Sheath Blight and Bacterial Panicle Blight of Rice. PLoS One. Jan. 14;11(1):e0146764.
Smirnov, V.V., et al. (1997). Fluviols, bicyclic nitrogen-rich antibiotics produced by Pseudomonas fluorescens. FEMS Microbiology letters. 153:357-361.
Suarez-Moreno ZR, et al., 2019. Plant-Growth Promotion and Biocontrol Properties of Three *Streptomyces* spp. Isolates to Control Bacterial Rice Pathogens. Front Microbiol 10, 290.
Sundin GW, et al, 2016. Bacterial disease management: challenges, experience, innovation and future prospects: Challenges in Bacterial Molecular Plant Pathology. Mol Plant Pathol 17, 1506-18.
Thomashow LS, et al, 1988. Role of a phenazine antibiotic from Pseudomonas fluorescens in biological control of *Gaeumannomyces graminis* var. tritici. J Bacteriol 170, 3499-508.
Trippe, K., et al. (2013). Pseudomonas fluorescens SBW25 produces furanomycin, a non-proteinogenic amino acid with selective antimicrobial properties. BMC Microbioloy. 13:111.
Upadhyay, A., et al. (2008). Characterization of a new isolate of Pseudomonas fluorescens strain Psd as a potential biocontrol agent. Lett. Appl. Microbiol. 47(2):98-105.
Voisard C, et al, 1989. Cyanide production by Pseudomonas fluorescens helps suppress black root rot of tobacco under gnotobiotic conditions. EMBO J 8, 351-8.
Weller DM, 2007. Pseudomonas biocontrol agents of soilborne pathogens: looking back over 30 years. Phytopathology 97, 250-6.
Wilkinson, K.A. et al. Prospecting for Biological Control Agents against Burkholderia glumae, the causal agent of bacterial panicle blight of rice. Poster presented at American Phytopathological Society—95th Southern Division Meeting. Feb. 16-18, 2018.
Yasmin S, et al., 2016. Plant Growth Promotion and Suppression of Bacterial Leaf Blight in Rice by Inoculated Bacteria. PLoS One 11, e0160688.
Yendyo, S., et al. (2017). Evaluation of *Tricoderma* spp., Pseudomonas fluorescens and Bacillus subtilis for biological control of Ralstonia wilt of tomato. F100Res.6:2020.

* cited by examiner

FIG. 1A
FIG. 1B
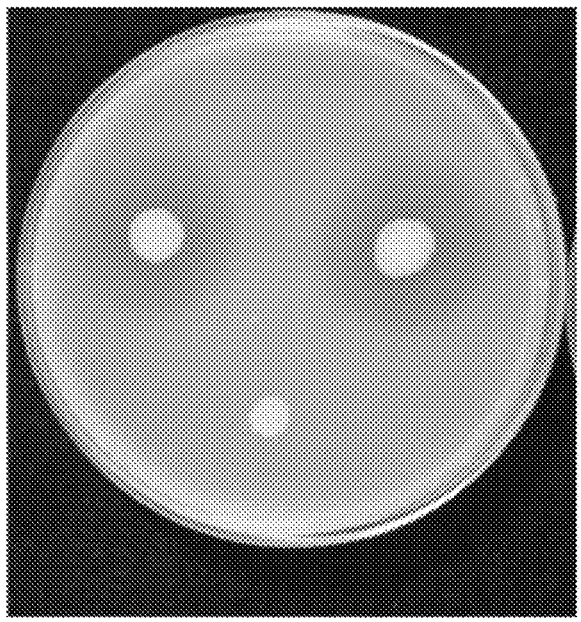
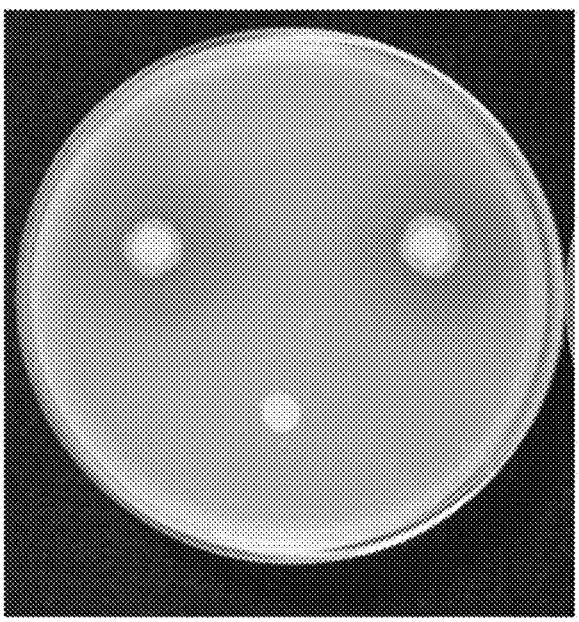
*Pseudomonas fluorescens*
*Burkholderia cenocepacia*

FIG. 5A
30 kDa

Pf >30kD + B. glumae   Pf <30kD + B. glumae   KB + H₂O + B. glumae

FIG. 5B
10kD

Pf >10kD + B. glumae   Pf <10kD + B. glumae   KB + H₂O + B. glumae

BURKHOLDERIA CENOCEPACIA AND PSEUDOMONAS FLUORESCENS COMPOSITIONS AND METHODS OF USING THE SAME

CROSS-REFERENCE TO RELATED APPLICATIONS

This patent application claims the benefit of priority of United States Provisional Patent Application No. 62/727, 095, filed Sep. 5, 2018, which is incorporated herein by reference in its entirety.

INTRODUCTION

Control of plant diseases is crucial to the reliable production of food. Disease control may be achieved by several routes, including the production of disease-resistant plants, cultivation techniques such as crop rotation, and pesticide use. Nonetheless, it is estimated that diseases reduce plant yields by roughly 10% every year in more developed settings, and often by greater than 20% in less developed settings. Thus, plant diseases cause major economic losses for farmers worldwide, and there is a continuing need for improved methods for disease control.

Bacterial panicle blight (BPB) of rice is one example of a devastating plant disease for which improved treatments are in demand. BPB is an emergent disease in the United States that has been problematic in Asia and Latin America. In the United States, BPB caused huge losses in rice yields in Arkansas over the past 25 years. BPB is caused by the bacterial pathogen *Burkholderia glumae* and, currently, there are no effective treatments against this pathogen.

SUMMARY

In one aspect of the present invention, new strains of *Pseudomonas fluorescens* and *Burkholderia cenocepacia* are provided. A new *Pseudomonas fluorescens* strain designated as PBL13 is provided. A viable culture of PBL13 is deposited in the ARS Culture Collection (NRRL), Peoria, Ill. under the accession number B-68083. A new *Burkholderia cenocepacia* strain designated as PBL18 is provided. A viable culture of PBL18 is deposited in the American Type Culture Collection (ATCC) under the accession number PTA-127637.

In another aspect, the present invention relates to secreted fraction compositions from the bacterial strains *Pseudomonas fluorescens* PBL13 and *Burkholderia cenocepacia* PBL18. The secreted fraction compositions may be produced by a method including culturing the bacterial strains described herein in a growth medium capable of supporting the growth of the bacterial strains to produce a bacterial culture composition, and separating the supernatant of the bacterial culture composition from the bacteria to produce the secreted fraction composition. Alternatively, the bacterial secreted fraction compositions may be produced by a method including culturing the bacterial strains on a solid growth medium, such as an agar and recovering the secreted fraction from the solid media after growth of the bacteria. Optionally, the secreted fraction compositions may be subjected to size selection.

In a further aspect, the present invention relates to agricultural compositions. The agricultural compositions may include any of the *Pseudomonas fluorescens* or *Burkholderia cenocepacia* strains described herein and a carrier. Alternatively, the agricultural compositions may include any of the *Pseudomonas fluorescens* secreted fraction compositions or *Burkholderia cenocepacia* secreted fraction compositions described herein and a carrier.

In an additional aspect, the present invention relates to plants treated with the bacterial strains, secreted fraction compositions, or agricultural compositions of the present invention.

In another aspect of the present invention, methods for inhibiting the growth of a microorganism are provided. In some embodiments, the microorganism is a plant pathogen and the growth of the microorganism on a plant is inhibited. The methods may include contacting the plant with an effective amount of any of the *Pseudomonas fluorescens* or *Burkholderia cenocepacia* strains described herein, any of the *Pseudomonas fluorescens* secreted fraction compositions or *Burkholderia cenocepacia* secreted fraction compositions described herein, or any of the agricultural compositions described herein to inhibit the growth of the microorganism. In one embodiment, the growth of the microorganism on the plant is inhibited.

In a further aspect of the present invention, methods of producing a secreted fraction composition are provided. The methods may include culturing any of the bacterial strains described herein in a growth medium capable of supporting the growth of the bacterial strain to produce a bacterial culture composition, and separating the bacteria from the growth medium to produce the secreted fraction composition. The growth medium may be a liquid growth medium or an agar-based plate growth medium. If a liquid growth medium is used the secreted fraction may be separated by collecting the supernatant of the bacterial growth medium. Alternatively, the material secreted into the agar solid growth medium may be separated to collect the secreted fraction composition. Optionally, the methods may further include lyophilizing the secreted fraction composition, or separating the secreted fraction composition by molecular size to produce a size selected secreted fraction. Suitably the size selected secreted fraction includes molecules under 10 kD or above 30 kD.

BRIEF DESCRIPTION OF DRAWINGS

FIGS. 1A-1F show that *Burkholderia cenocepacia* PBL18 and *Pseudomonas fluorescens* PBL13 inhibit the growth of a broad range of pathogens in vitro. FIGS. 1A-1D show inhibition of several bacterial strains. Here, liquid cultures of 25 bacterial strains were mixed with molten King's B (KB) to a final concentration of OD600=0.01 and poured onto petri plates. Sterile filter paper disks containing five microliters of *P. fluorescens* PBL13 (FIG. 1A, FIG. 1C) or *B. cenocepacia* PBL18 (FIG. 1B, FIG. 1D) at a concentration of OD600=1 were placed on the solidified agar and incubated at 30° C. Zones of inhibition were observed after 48 h. FIGS. 1A-1B show images of the plates containing *Burkholderia glumae* culture after 48 h. FIGS. 1C-1D show bar graphs of the average areas of zone inhibition, measured using ImageJ, and the standard deviation for three experiments containing three replications each. Letters above the bars indicate statistical significance using Tukey's range test. Same letters in different bars indicate no statistically significant difference among them. FIGS. 1E-1F show inhibition of several fungi. Here, two plugs of fungal mycelia were placed on the surface of Malt Extract Agar and *B. cenocepacia* PBL18 or *P. fluorescens* PBL13 were placed in the middle of the plate. Plates were incubated at 27° C. and fungal growth was measured after 48 hours. FIG. 1E shows images of plates containing fungi after 48 h. FIG. 1F shows a bar graph of the percentage of fungal growth, calculated by measuring the radius of fungal growth in the presence of *B. cenocepacia* PBL18 or *P. fluorescens* PBL13, divided by the respective fungal growth without *B. cenocepacia* or *P. fluorescens*. Three independent experiments were conducted.

Figure 2:
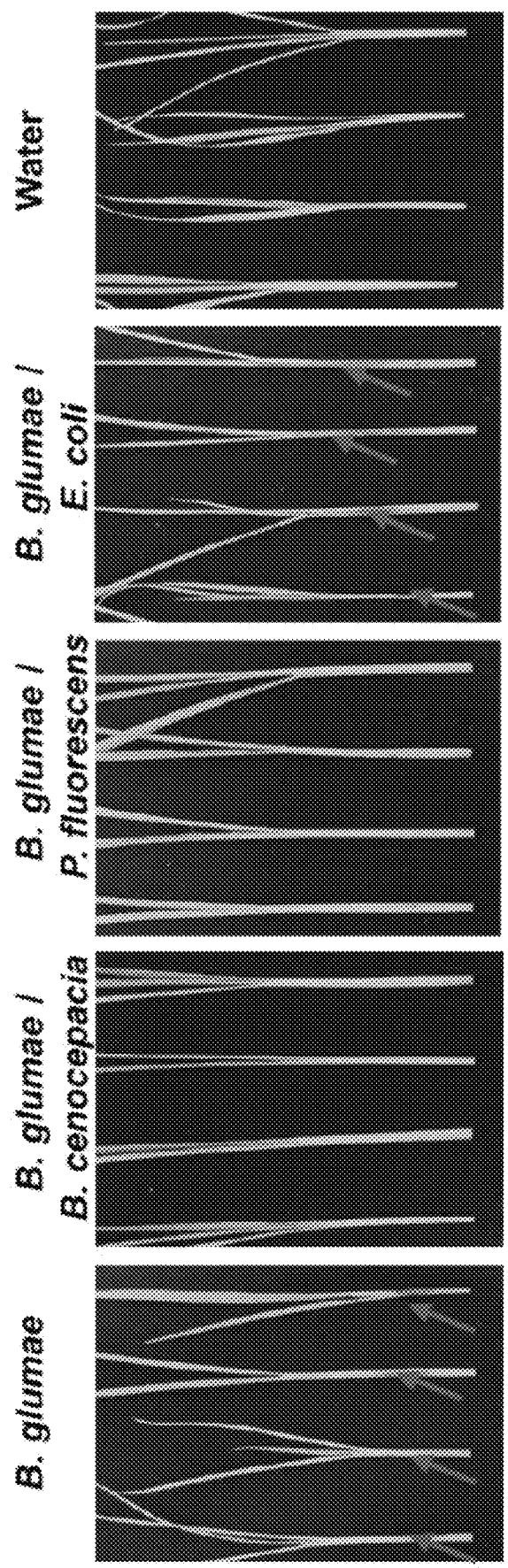

FIG. 2 shows co-inoculation of *B. glumae* with either *P. fluorescens* PBL13 or *B. cenocepacia* PBL18 inhibits disease symptoms in rice. Six-week-old rice plants from cultivar Wells (a susceptible cultivar) were inoculated in the stem with *B. glumae* alone or with *B. glumae* combined with either *B. cenocepacia* PBL18, *P. fluorescens* PBL13, or *E. coli*. Plants inoculated with *B. glumae* alone showed disease symptoms in the stem characterized by brown lesions surrounding the area of inoculation (red arrows). However, plants that were inoculated with the combinations of *B. glumae*/*P. fluorescens* PBL13 or *B. glumae*/*B. cenocepacia* PBL18 did not have any disease symptoms. This effect can be directly attributed to these bacterial strains as plants inoculated with the combination *B. glumae*/*E. coli* still had disease symptoms that resemble the symptoms observed by *B. glumae* alone.

Figure 3:
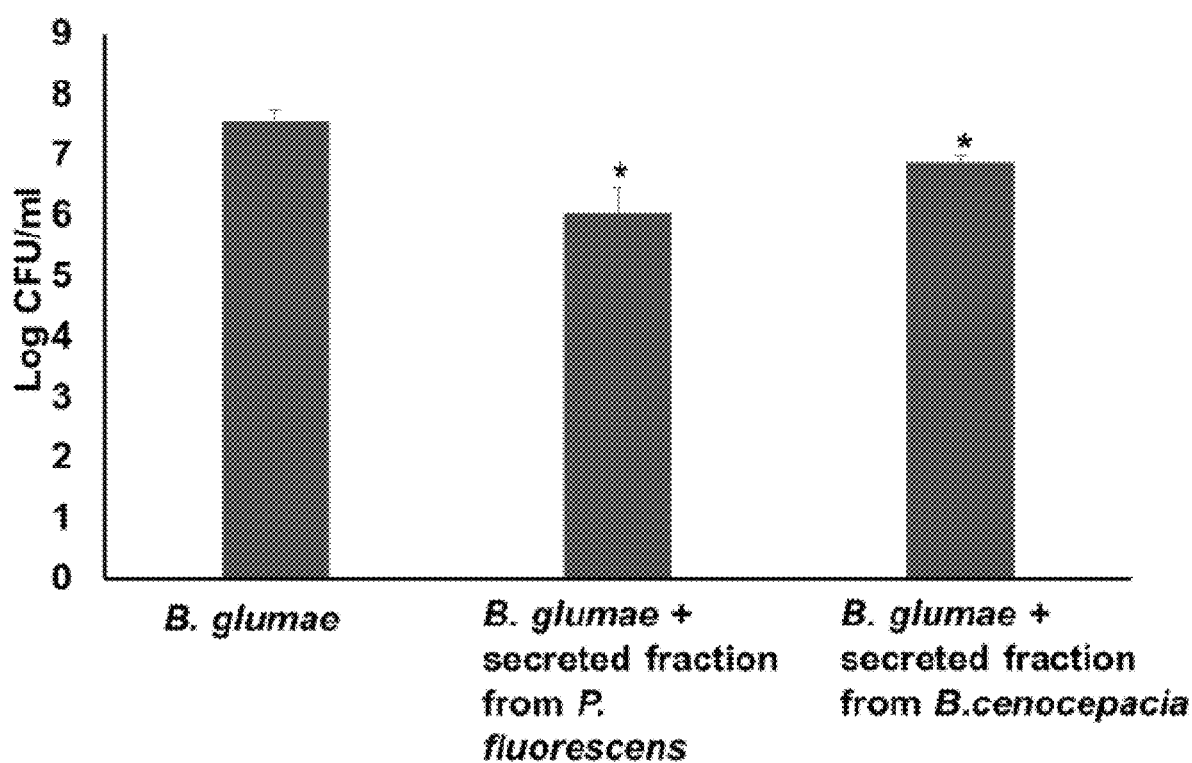

FIG. 3 shows secreted fractions from *P. fluorescens* PBL13 and *B. cenocepacia* PBL18 reduce *B. glumae* growth. To obtain a soluble fraction of inhibitory compounds, agar squares from the zone of inhibition were transferred to sterile water or King's B (KB) media broth and shaken at 30° C. for 18 h. Water and KB were filtered-sterilized to eliminate potentially contaminating bacteria and mixed with KB broth in a 1:1 (volume:volume) ratio. KB alone or mixed with water containing soluble potentially inhibitory compounds was used to grow a single colony of *B. glumae*. After 18 h of growth, cultures of *B. glumae* were serially diluted and plated to enumerate bacteria. Bars represent growth of *B. glumae* in KB broth alone or in KB supplemented with soluble fractions derived from *P. fluorescens* PBL13 or *B. cenocepacia* PBL18. Asterisks above bars indicate statistically significant difference when compared with *B. glumae* alone using Student's T-Test ($P<0.01$).

Figure 4:
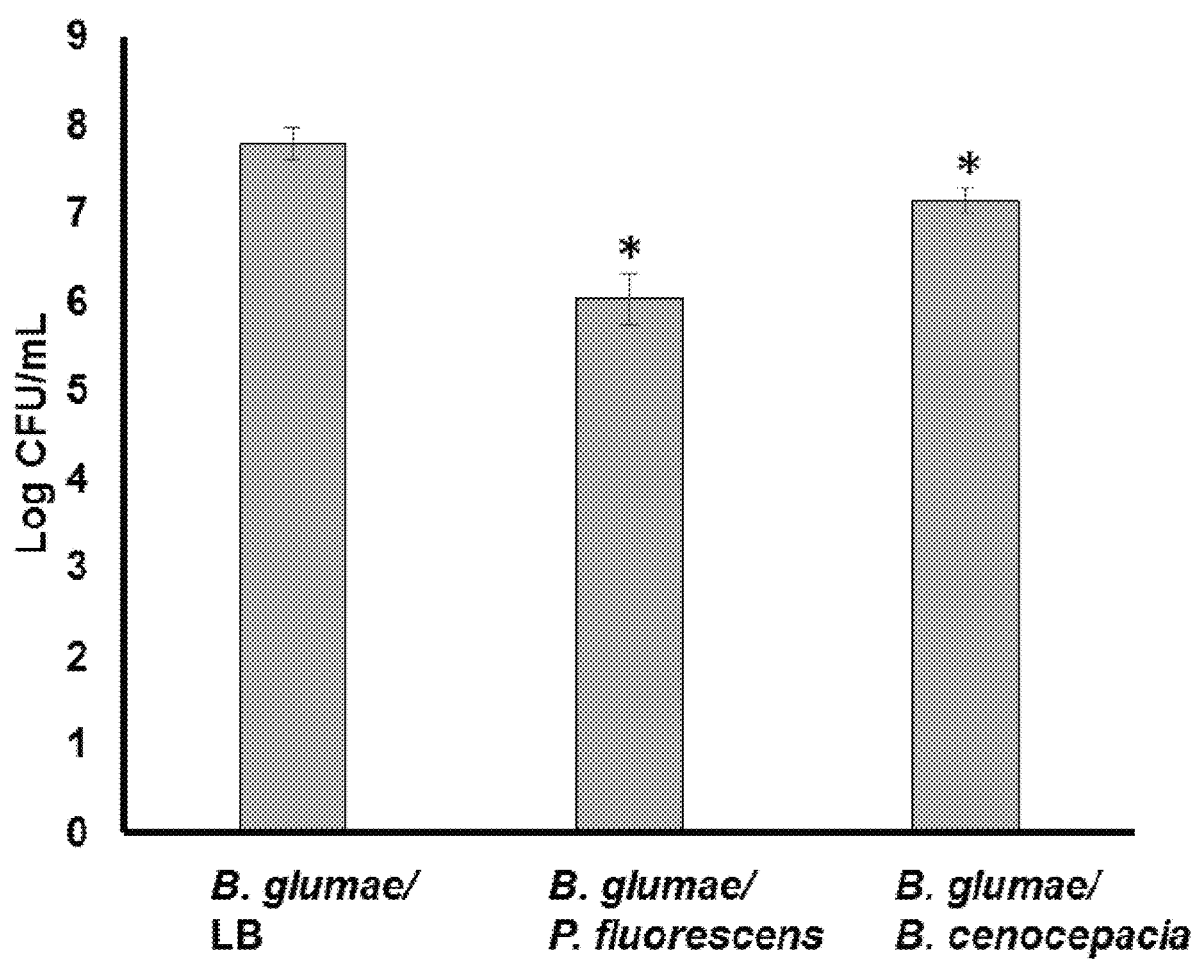

FIG. 4 shows lyophilized supernatants from *P. fluorescens* PBL13 and *B. cenocepacia* PBL18 reduce growth of *B. glumae*. *P. fluorescens* PBL13 and *B. cenocepacia* PBL18 were grown in 1 L of LB broth at 30° C. with constant agitation for 18 h. Bacterial cultures were centrifuged at 6,000 rpm for 15 min at room temperature and supernatants were transferred to 50 ml conical tubes and lyophilized for 2 days. Pure LB broth was also lyophilized. Lypholized LB broth and bacterial supernatants were diluted to 0.01 g/1 mL in sterile water, filter sterilized and used to amend KB broth by mixing it in 1:1 (volume:volume) ratio. These mixtures were further used to grow a single colony of *B. glumae*. After 18 h of growth, cultures of *B. glumae* were serially diluted and plated to enumerate bacteria. Bars represent growth of *B. glumae* in KB broth alone or in KB supplemented with lyophilized fractions derived from *P. fluorescens* or *B. cenocepacia*. Asterisks above bars indicate statistically significant difference when compared with *B. glumae* alone using Student's T-Test ($P<0.01$).

FIGS. 5A-5B show that there are multiple growth inhibitory activities in the secreted fractions of *P. fluorescens*. Secreted fractions from *P. fluorescens* were obtained as previously described and lyophilized for three days. One gram of lyophilized secreted fraction was reconstituted in 10 ml of sterile water and concentrated using concentrators of 30,000 molecular weight cutoff (30 kDa) (FIG. 5A) or 10,000 molecular weight cutoff (10 kDa) (FIG. 5B). Two hundred microliters of the fractions above and below the molecular weight cutoff were filtered sterilized using a 0.22 μM filter and mixed with 200 μl of KB broth. One colony of *B. glumae* was added to each tube and grown for 24 h at 28° C. with constant agitation. After 24 h, samples were serially diluted and plated to enumerate bacteria. Bars represent the growth of *B. glumae* in KB mixed with fractions of different molecular weight cutoffs or the growth of *B. glumae* in KB mixed with water.

Figure 6:
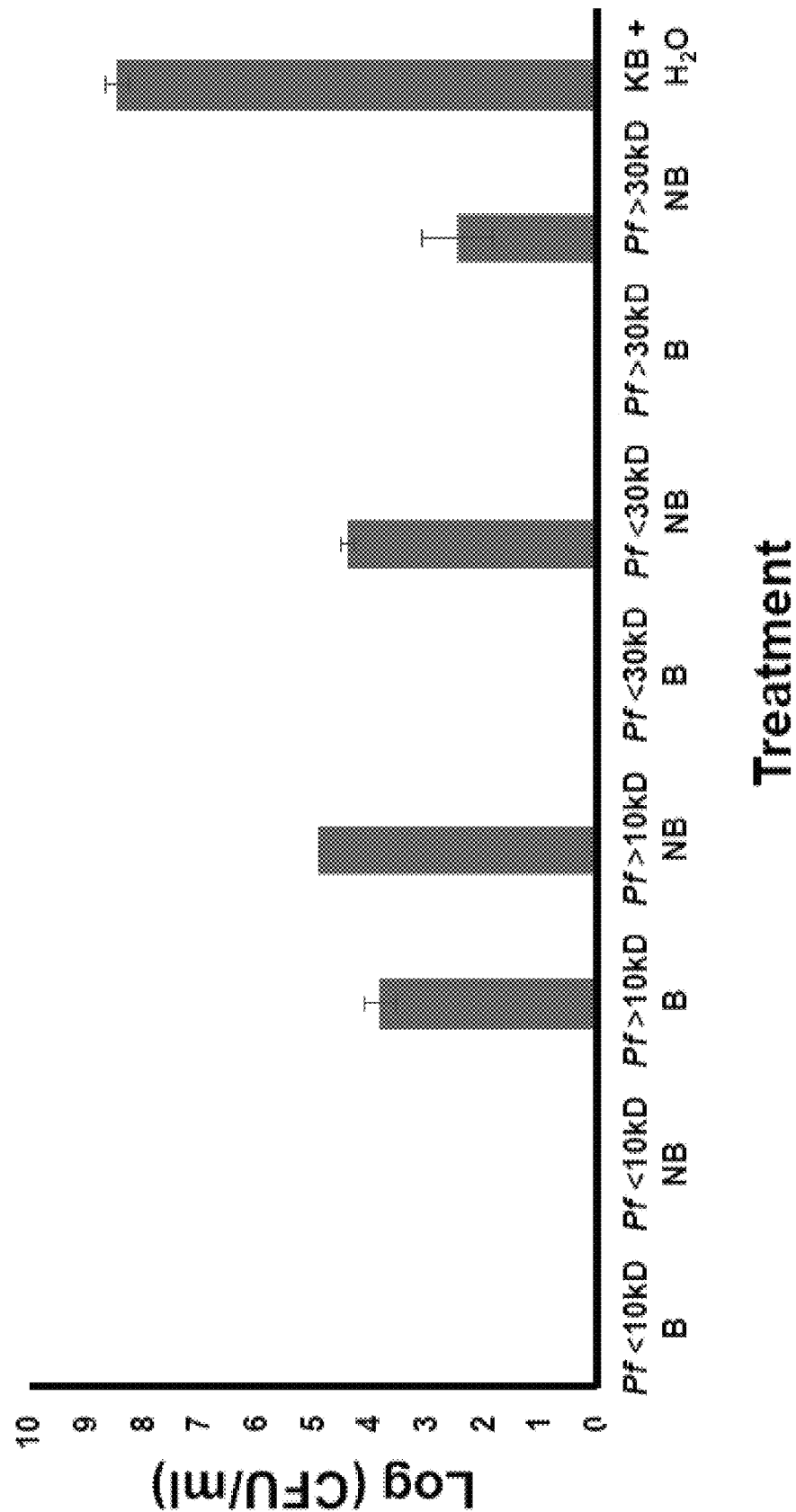

FIG. 6 shows that boiling does not adversely affect the activity of the fractions below 10 kDa but may enhance the activity of the fractions above 10 kDa and above or below 30 kDa. Lyophilized secreted fractions separated by concentrators with 30,000 and 10,000 molecular weight cutoffs were divided into two pools and one of the pools was boiled. Two hundred microliters of boiled (B) and non-boiled (NB) samples were mixed with 200 μl of KB broth and used to grow a single colony of *B. glumae*. Bars represent the growth of *B. glumae* in KB mixed with the fractions of different molecular weight cutoffs, either boiled (B) or non-boiled (NB), or the growth of *B. glumae* in KB mixed with water.

DETAILED DESCRIPTION

Here, in the non-limiting Examples, the present inventors have discovered that new strains of *Pseudomonas fluorescens* and *Burkholderia cenocepacia* secrete antimicrobials that inhibit the growth, for example, of the rice pathogen *Burkholderia glumae*, the main causative agent of bacterial panicle blight (BPB) in rice. These antimicrobials thus represent a potential solution to control a disease affecting an economically important crop that is a staple for a large human population and are also effective against other microbial species.

After screening a laboratory collection containing bacterial strains isolated from fields of Arkansas, the present inventors discovered that one strain of *Burkholderia cenocepacia* (designated as PBL18) and one strain of *Pseudomonas fluorescens* (designated as PBL13) inhibited the growth of the rice pathogen *Burkholderia glumae* on petri plates. Moreover, when the *Burkholderia cenocepacia* PBL18 or *Pseudomonas fluorescens* PBL13 were mixed with *Burkholderia glumae* and, these mixtures were used to infiltrate rice plants, the symptoms of the disease were reduced or eliminated, and that effect was not observed in a control experiment that included an infiltration of rice by a mixture of *Burkholderia glumae* and *Escherichia coli*.

The inventors also demonstrated that the *Burkholderia cenocepacia* PBL18 and *Pseudomonas fluorescens* PBL13 strains inhibit the growth of several additional plant pathogens, including bacterial pathogens from the genera *Burkholderia*, *Xanthomonas*, and Envinia, as well as fungal pathogens from the genera *Rhizoctonia*, *Pythium*, *Magnaporthe*, and *Fusarium*. Interestingly, the present inventors also demonstrate cell-free preparations from the identified strains of *Burkholderia cenocepacia* and *Pseudomonas fluorescens* reduced the growth of *Burkholderia glumae*, indicating that the growth inhibition can be obtained even in the absence of bacteria and that the bacteria secrete inhibitory compounds. Obtaining secreted fractions with antimicrobial activities against *Burkholderia glumae* may allow scaling up production of these antimicrobials and will pave the way towards controlling bacterial panicle blight of rice.

Finally, to characterize of the secreted fractions of *P. fluorescens*, the inventors separated the secreted fractions by molecular size using two different concentrators, and found that while all the fractions had inhibitory activity, the fraction that included molecules with a molecular weight below 10 kDa completely inhibited the growth of *B. glumae*.

Compositions

In one aspect of the present invention, new strains of *Pseudomonas fluorescens* and *Burkholderia cenocepacia* are provided. A new *Pseudomonas fluorescens* strain designated as PBL13 is provided. A viable culture of PBL13 is deposited in the ARS Culture Collection (NRRL), Peoria, Ill. under the accession number B-68083. A new *Burkholderia cenocepacia* strain designated as PBL18 is provided. A viable culture of PBL18 is deposited in the American Type Culture Collection (ATCC) under the accession number PTA-127637.

In another aspect, the present invention relates to *Pseudomonas fluorescens* PBL13 secreted fraction compositions. The *Pseudomonas fluorescens* secreted fraction compositions may be produced by a method including culturing the *Pseudomonas fluorescens* strain PBL13 described herein in a growth medium capable of supporting the growth of the *Pseudomonas fluorescens* strain to produce a *Pseudomonas fluorescens* culture composition, and separating the supernatant/secreted components in the growth media present after the culturing period of the *Pseudomonas fluorescens* culture composition to produce the *Pseudomonas fluorescens* secreted fraction. Optionally, the *Pseudomonas fluorescens* secreted fractions may be separated by molecular size, preferably to select for a molecular weight below 10 kDa. In another aspect, the present invention relates to *Burkholderia cenocepacia* PBL18 secreted fraction compositions. The *Burkholderia cenocepacia* secreted fraction compositions may be produced by a method including culturing the *Burkholderia cenocepacia* PBL18 strain described herein in a growth medium capable of supporting the growth of the *Burkholderia cenocepacia* strain to produce a *Burkholderia cenocepacia* culture composition, and separating the supernatant/secreted components in the growth media present after the culturing period of the *Burkholderia cenocepacia* culture composition to produce the *Burkholderia cenocepacia* secreted fraction.

Two methods were used to prepare the cell-free secreted fractions used herein, but other suitable methods may be used to generate the compositions described herein. The bacteria may be grown on agar plates, such as King's B agar, and 5 mm agar squares can be removed from the zone of inhibition and transferred to 3 ml of sterile water and shaken in a 30° C. incubator for 18 hr followed by filter sterilization using a 0.22 µM filter to remove bacteria or remaining agar to obtain the secreted fraction. In a second method the bacteria may be grown in 100 mL of broth, such as Luria Bertani (LB) broth, for 18 hr at 30° C. in a shaker incubator. The cultures were centrifuged for 10 minutes at 6,000 rpm and the supernatant was collected. The centrifuged supernatants were aliquoted such that 20 mL was added to each 50 mL flasks and lyophilized for 24 hr. The lyophilized supernatants were resuspended in sterile water and filter sterilized using a 0.22 µM filter to remove bacteria. Growth media capable of supporting the growth of *Pseudomonas fluorescens* or *Burkholderia cenocepacia* are generally known in the art. For example, the growth media may be LB. Media containing a source of nitrogen, amino acids, vitamins and trace minerals may be used.

As used herein, a "supernatant" refers to the liquid portion apart from the solid residue in a sample. The supernatant may be "isolated" or "separated" from a sample, i.e. a culture, by, for example, processing the sample with a technique including, without limitation, centrifugation, precipitation, filtration or other processes.

In a further aspect, the present invention relates to agricultural compositions. An "agricultural composition" is a composition formulated for application to a plant or plant part, such as a seed. An agricultural composition is commonly in liquid form (i.e., liquid suspension) for application by spraying or soaking, but may be in a solid, granular, or powder form for rehydration or application by dusting or dry coating. The agricultural composition may be concentrated, for example by lyophilization, for dilution in water or other solvent. The agricultural compositions may be prepared for administration to plants or may be prepared for administration to seeds.

The agricultural compositions may include any of the *Pseudomonas fluorescens* or *Burkholderia cenocepacia* strains described herein or a combination thereof and a carrier. The agricultural compositions may also include any of the *Pseudomonas fluorescens* secreted fraction compositions or *Burkholderia cenocepacia* secreted fraction compositions described herein, or combinations thereof and a carrier. As used herein, a "carrier" may be solid or liquid and may include substances ordinarily employed in formulations applied to plants. Carriers may include a buffer, water, oil, nonionic surfactants, ionic surfactants such as cationic or anionic surfactants, or available agricultural by-products from, for example and without limitation, rice. In some embodiments, the agricultural compositions may also include an additional active ingredient such as, without limitation, a fungicide, an herbicide, an insecticide, a biosanitizer product or fertilizer.

The agricultural compositions may include any of the *Pseudomonas fluorescens* strains described herein at a concentration between $10^5$ to $10^{12}$ or more cfu per milliliter or any range therein. Suitably, the concentration of the *Pseudomonas fluorescens* PBL13 strain in the agricultural composition may be $10^7$ to $10^{10}$ cfu per milliliter or between $10^8$ and $10^9$ cfu per milliliter.

The agricultural compositions may include any of the *Burkholderia cenocepacia* strains described herein at a concentration between $10^5$ to $10^{12}$ or more cfu per milliliter or any range therein. Suitably, the concentration of the *Burkholderia cenocepacia* PBL18 strain in the agricultural composition may be $10^7$ to $10^{10}$ cfu per milliliter or between $10^8$ and $10^9$ cfu per milliliter.

In a further aspect of the present invention, plants treated with the compositions described herein are provided. The plants may be treated with any of the *Pseudomonas fluorescens* or *Burkholderia cenocepacia* strains described herein, any of the *Pseudomonas fluorescens* secreted fraction compositions or *Burkholderia cenocepacia* secreted fraction compositions described herein, or any of the agricultural compositions described herein. The *Pseudomonas fluorescens* or *Burkholderia cenocepacia* strains described herein, the *Pseudomonas fluorescens* secreted fraction compositions or *Burkholderia cenocepacia* secreted fraction compositions described herein, or the agricultural compositions described herein may be present on or within at least a part of the plant. The treated plants are more resistant to disease causing bacteria and fungi as described herein and shown in the Examples.

As used herein, a "plant" includes any portion of the plant including, without limitation, a whole plant or a portion of a plant such as a part of a root, leaf, stem, seed, pod, flower, cell, tissue plant germplasm, asexual propagate, or any progeny thereof. For example, a rice plant refers to the whole rice plant or portions thereof including, without limitation, the leaves, roots, seeds or otherwise. Suitable "plants" may include, without limitation, rice, tomato, onion, cotton, soybean, wheat, ryegrass, crucifers, prunus, beans, kiwi fruit, mango, apple, pear, sunflower, maple, European horse chestnut, Indian horse chestnut, beet, hazelnut, barley, cucumber, cabbage, mulberry, cherry, millet, pea, olive, tobacco, camellia, sorghum, or corn. In some embodiments, the plant is a rice plant.

Methods

In another aspect of the present invention, methods for inhibiting the growth of a microorganism on a plant are provided. The methods may include contacting the plant with an effective amount of any of the *Pseudomonas fluorescens* or *Burkholderia cenocepacia* strains described herein, any of the *Pseudomonas fluorescens* secreted fraction compositions or *Burkholderia cenocepacia* secreted fraction compositions described herein, any of the agricultural compositions described herein or combinations thereof to inhibit the growth of the microorganism on the plant.

The "microorganism" whose growth is inhibited by the methods or specifically by the secreted fraction compositions described herein may be any microorganism, preferably a plant pathogen. Suitably, the microorganism is a bacterium or fungus, including, without limitation, a bacterium of the genera *Burkholderia, Xanthomonas*, or *Erwinia*, or a fungus of the genera *Rhizoctonia, Pythium, Magnaporthe*, or *Fusarium*. In some embodiments, the microorganism is *Burkholderia glumae*.

As used herein, "contacting" may be carried out through any of the variety of procedures used to apply compositions to plants that will be apparent to the skilled artisan. Suitable application methods may include, without limitation spraying or dusting. Other suitable application procedures can be envisioned by those skilled in the art. Contacting may also be carried out indirectly via application, for example, to the soil surrounding a plant, via trunk injection, or other plant media or substrates. The "contacting" of the present methods may be carried out before or after the microorganism grows on the plant.

In the present methods, various parts of the plant may be contacted with the *Pseudomonas fluorescens* or *Burkholderia cenocepacia* strains described herein, the *Pseudomonas fluorescens* secreted fraction compositions or *Burkholderia cenocepacia* secreted fraction compositions described herein, the agricultural compositions described herein or combinations thereof. Suitably and without limitation, the leaves or seeds of the plant may be contacted with the *Pseudomonas fluorescens* or *Burkholderia cenocepacia* strains described herein, the *Pseudomonas fluorescens* secreted fraction compositions or *Burkholderia cenocepacia* secreted fraction compositions described herein, the agricultural compositions described herein or combinations thereof.

In some embodiments, the plant may be contacted at least 2, 3, 4, 5, or more times with with the *Pseudomonas fluorescens* or *Burkholderia cenocepacia* strains described herein, the *Pseudomonas fluorescens* secreted fraction compositions or *Burkholderia cenocepacia* secreted fraction compositions described herein, the agricultural compositions described herein or with combinations thereof. For example, the seeds of the plant could be treated with the strains prior to planting and then the secreted fractions or agricultural compositions could be sprayed onto the growing plants at one or more stage of development. The methods may be used as a preventative measure or may be used only on plants or in fields that microbial damage is suspected or noted.

"Effective amount" is intended to mean an amount of a composition described herein sufficient to inhibit the growth of a microorganism on a plant by, for example, 10%, 20%, 50%, 75%, 80%, 90%, 95%, or 1-fold, 3-fold, 5-fold, 10-fold, 20-fold, or more compared to a negative control. In some embodiments, the effective amount of the *Pseudomonas fluorescens* or *Burkholderia cenocepacia* strains (whether or not in an agricultural composition) may be $10^5$ to $10^{12}$ or more cfu per milliliter or any range therein. Suitably, the concentration of the *Pseudomonas fluorescens* or *Burkholderia cenocepacia* strains either alone or in an agricultural composition is $10^1$ to $10^{10}$ cfu per milliliter or between $10^8$ and $10^9$ cfu per milliliter.

A "negative control" refers to a sample that serves as a reference for comparison to a test sample. For example, a test sample can be taken from a test condition including the presence of a *Pseudomonas fluorescens* or *Burkholderia cenocepacia* strain and compared to negative control samples lacking these strains or including a composition not expected to inhibit microbial growth. One of skill in the art will recognize that controls can be designed for assessment of any number of parameters.

In a further aspect of the present invention, methods of producing a *Pseudomonas fluorescens* PBL13 or a *Burkholderia cenocepacia* PBL18 secreted fraction are provided. The methods may include culturing any of *Pseudomonas fluorescens* or *Burkholderia cenocepacia* strains described herein in/on a growth medium capable of supporting the growth of the *Pseudomonas fluorescens* strain or the *Burkholderia cenocepacia* strain to produce a *Pseudomonas fluorescens* or *Burkholderia cenocepacia* culture composition, and separating the supernatant/secreted fraction of the culture composition from the bacteria to produce the secreted fraction. Optionally, the methods may further include lyophilizing or applying a size selection to the secreted fraction. Size selection is a standard practice used by those of skill in the art. In the Examples, size selection is performed using two concentrators with distinct molecular weight cutoffs (10 kDa and 30 kDa). However, any method of size-based fractionation may be used with the present invention, including chromatographic and electrophoretic methods. As shown in the Examples, there was an active component capable of inhibiting the growth of microbial pathogens in the secreted fraction having a molecular weight of less than 10 kD that was more potent than any of the components remaining in the portion of the secreted fraction having molecular weights larger than 10 kD. These active components did not seem susceptible to boiling and thus are quite stable and may be useful in agricultural compositions to control microbial infections.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

*Pseudomonas fluorescens* and *Burkholderia cenocepacia* have a Broad Spectrum of Inhibitory Activity Against Plant Pathogenic Bacteria, Oomycetes and Fungi.

Two bacterial strains of the genera *Pseudomonas fluorescens* (PBL13) and *Burkholderia cenocepacia* (PBL18) were discovered and found to inhibit the growth of the rice bacterial pathogen *Burkholderia glumae* grown in Petri plates (FIGS. 1A-1B). Growth inhibition was observed as clear halos around filter disks containing *P. fluorescens* (FIG. 1A) or *B. cenocepacia* (FIG. 1B). Notably, several other strains of bacteria were tested that were not able to inhibit *B. glumae* growth.

To determine whether *Burkholderia cenocepacia* and *Pseudomonas fluorescens* have activity against other bacteria, the ability of these strains to inhibit the growth of various plant pathogenic bacteria from genera including *Burkholderia*, *Pseudomonas* and *Xanthomonas*, as well as the opportunistic bacteria *Klebsiella pneumonia* was tested. As shown in FIG. 1C, *P. fluorescens* was very effective at inhibiting the growth of *B. glumae* and *B. gladioli*, as is reflected by the large areas of zone inhibition. *P. fluorescens* had a moderate effect on the growth of five strains of the genus *Burkholderia*, four of them belonging to *B. cenocepacia* complex. This moderate effect was also observed against Envinia amylovora. *P. fluorescens* also demonstrated some growth inhibition against *Xanthomonas*, though at low levels.

Figure 1D:
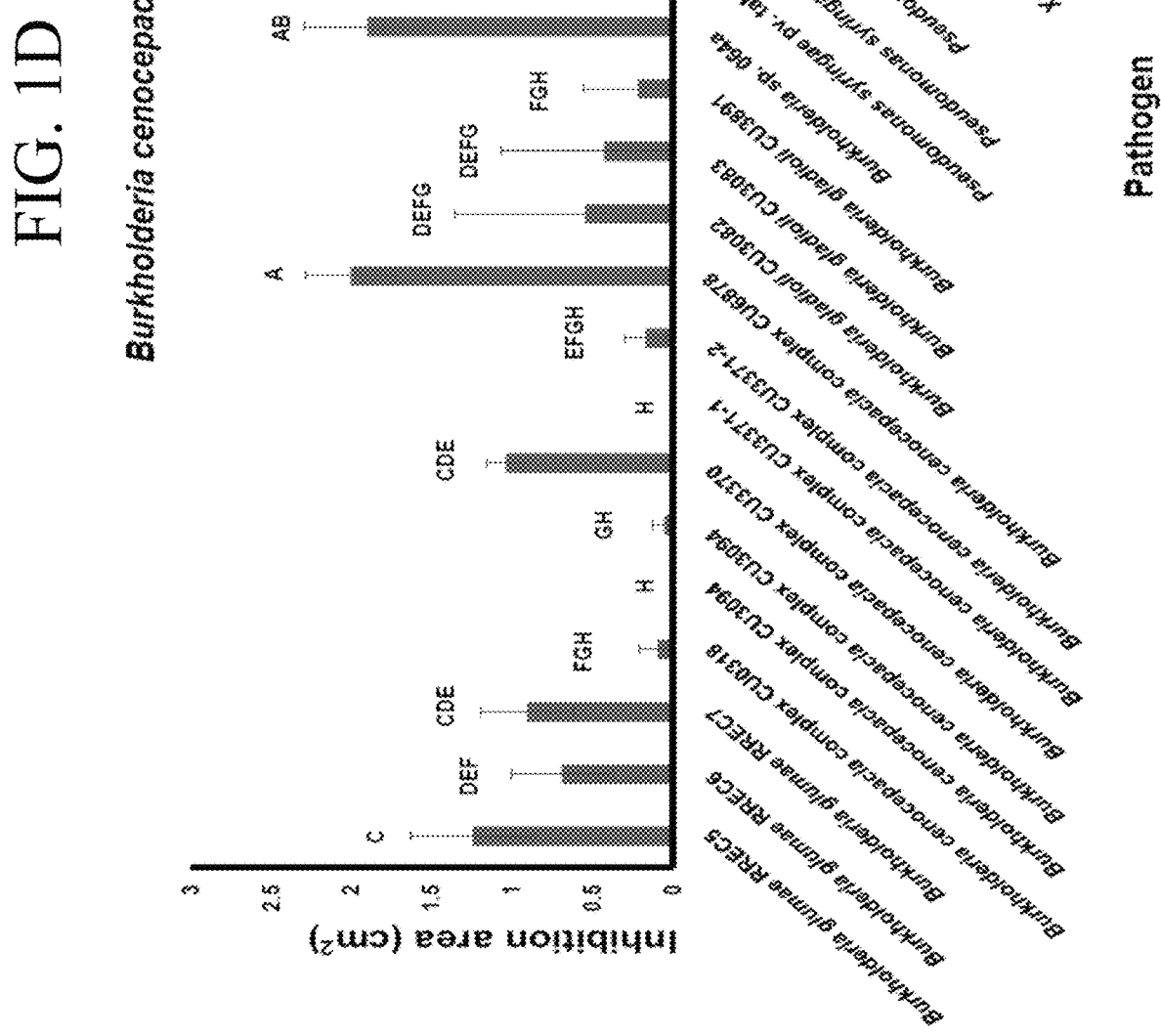

*B. cenocepacia* also inhibited the growth of several bacterial strains, but it was less effective than *P. fluorescens* (FIG. 1D). *B. cenocepacia* showed significant growth inhibition of *B. cenocepacia* complex CU6878 and *Burkholderia* sp 064a. Moderate levels of growth inhibition were observed towards other species of *Burkholderia*, *Pseudomonas syringae* pv. glycinea, *Erwinia amylovora*, *Xanthomonas campestris* pv. *malvacearum*, and other *Xanthomonas* sp.

Figure 1E:
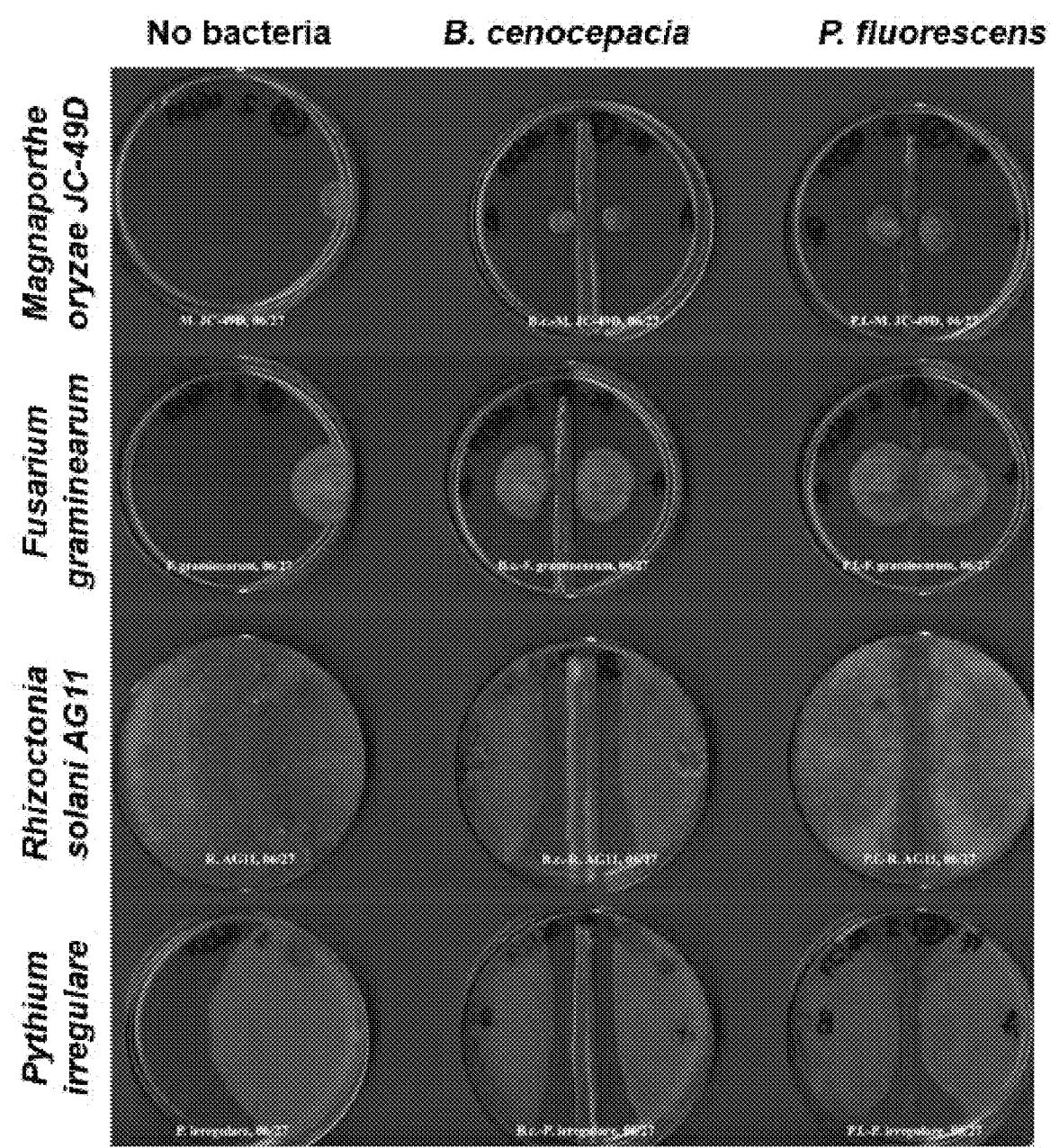
Figure 1F:
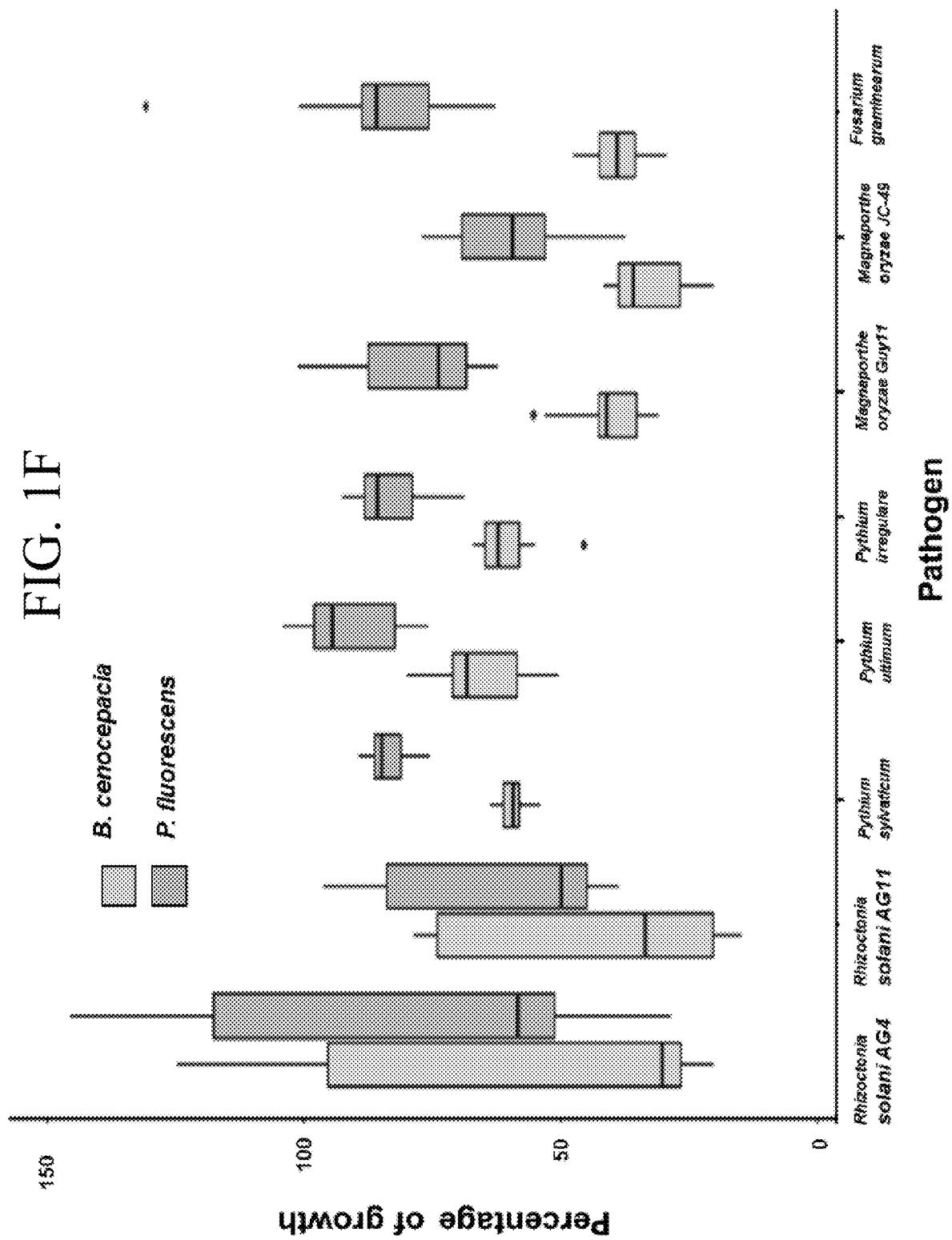

The effect of *B. cenocepacia* and *P. fluorescens* on the growth of fungal plant pathogens such as *Magnaporthe oryzae* JC-49D, *Fusarium graminearum*, *Rhizoctonia solani* AG-11 and the oomycete plant pathogen *Pythium irregular* was also evaluated. In these experiments *B. cenocepacia* or *P. fluorescens* were streaked as a line on the middle of the agar, and plugs containing fungal or oomycete mycelia were place on the two halves of the agar. *B. cenocepacia* and *P. fluorescens* inhibited the growth of *R. solani* AG11 and *P. irregulare* and the mycelial proliferation stopped before reaching the bacterial line (FIG. 1E). This assay was repeated with additional pathogens including *R. solani* AG4, *Pythium sylvaticum*, *Pythium ultimum* and *Magnaporthe oryzae* Guy 11. FIG. 1F shows that both *B. cenocepacia* and *P. fluorescens* reduce the growth of *R. solani* AG11, *P. sylvaticum*, *P. ultimum*, *P. irregulare*, *M oryzae* G-11, *M. oryzae* JC-49 and *F. graminearum*, although to different levels. In all cases, higher growth inhibition was observed with *B. cenocepacia* than with *P. fluorescens*. *B. cenocepacia* caused a 40% growth inhibition of *P. sylvaticum*, *P. ultimum* and *P. irregulare*, and caused a 70% growth inhibition of *Magnaporthe oryzae* and *F. graminearum*. *P. fluorescens* caused between 10 and 20% growth inhibition of *P. sylvaticum*, *P. ultimum* and *P. irregulare* and between 20 and 40% growth inhibition of *Magnaporthe oryzae* and *F. graminearum*.

*Pseudomonas fluorescens* and *Burkholderia cenocepacia* Control Bacterial Panicle Blight in Rice.

To determine whether these bacterial strains could be used to control the disease in rice, rice plants from cultivar Wells (a susceptible cultivar) were inoculated in the stem with *B. glumae* (the rice pathogen) alone or with *B. glumae* combined with either *P. fluorescens*, *B. cenocepacia*, or *E. coli* at a concentration of $10^8$ CFU/mL (FIG. 2). Plants inoculated with *B. glumae* alone showed disease symptoms in the stem characterized by brown lesions surrounding the area of inoculation. However, plants that were inoculated with the combinations of *B. glumae/P. fluorescens* or *B. glumae/B. cenocepacia* did not have any disease symptoms. This effect can be directly attributed to these bacterial strains as plants inoculated with the combination *B. glumae/E. coli* still had disease symptoms that resemble the symptoms observed by *B. glumae* alone.

*Pseudomonas fluorescens* and *Burkholderia cenocepacia* Secrete Compounds with Antimicrobial Activity.

Potential antimicrobials were eluted from the zones of growth inhibition (from FIGS. 1A-1B) and filter sterilized to obtain cell-free preparations that were further used to amend KB broth to culture *B. glumae* (FIG. 3), using non-amended KB broth as a control. *B. glumae* grown in KB broth alone reached significantly higher populations than *B. glumae* grown on KB amended with cell-free preparations derived from *P. fluorescens* or *B. cenocepacia*.

Cell-free preparations of the potential antimicrobials were also obtained using culture supernatants from *P. fluorescens* and *B. cenocepacia* that were further lyophilized to preserve the stability and, consequently activity of the potential antimicrobials. Lyophilized fractions were further used to amend Luria Berthani (LB) broth at a concentration of 0.01 g/mL to culture *B. glumae* (FIG. 4), using as control non-amended LB broth. *B. glumae* grown in KB broth alone reached significantly higher populations than *B. glumae* grown on KB amended with cell-free preparations derived from lyophilized supernatants obtained from *P. fluorescens* or *B. cenocepacia* cultures.

These data suggest *P. fluorescens* and *B. cenocepacia* secrete compounds with antimicrobial activity and that the antimicrobial activity can be captured using either compositions including the *Pseudomonas fluorescens* and *Burkholderia cenocepacia* strains identified herein or using cell-free secreted fractions from these strains.

Molecules of Different Sizes are Responsible for the Growth Inhibitory Activity of *P. fluorescens* Secreted Fractions on *B. glumae*.

To initiate the chemical characterization of the secreted fractions of *P. fluorescens*, the secreted fractions were separated by molecular size using two different concentrators: one with molecular weight cutoff of 30,000 (30 kDa) and another with molecular weight cutoff of 10,000 (10 kDa). Fractions above and below their respective molecular weight cutoffs were retrieved and used to amend KB broth that was used to grow a colony of *B. glumae*. As shown in FIG. 5A, the fraction that included molecules with molecular weight above 30 kDa reduced the growth of *B. glumae* by 7 logs, while the fraction that included molecules with a molecular weight below 30 kDa reduced the growth of *B. glumae* by 4 logs. In addition, the fraction that included molecules with a molecular weight above 10 kDa reduced the growth of *B. glumae* by 3 logs, while the fraction that included molecules with a molecular weight below 10 kDa completely inhibited the growth of *B. glumae* (FIG. 5B).

Molecules Responsible for the Growth Inhibitory Activity of *P. fluorescens* are Resistant to Boiling.

To narrow down possible chemical categories associated with the growth inhibitory activities of *P. fluorescens*, the following molecular size fractions were isolated: below 10 kDa, above 10 kDa, below 30 kDa, above 30 kDa. These fractions were divided into two pools, and one of the pools was boiled. The fraction containing molecules below 10 kDa completely inhibited the growth of *B. glumae* and that effect was not eliminated by boiling (FIG. 6). The fraction containing molecules above 10 kDa still inhibited the growth of *B. glumae* with the boiled fraction showing a reduction of growth of 4 logs, while the non-boiled fraction showed a reduction of 3 logs as shown above (FIG. 6). This result suggests that boiling does not affect and may even enhance the activity of this fraction. The fraction containing molecules with a molecular weight below 30 kDa showed a significant increase in activity after boiling and completely inhibited the growth of *B. glumae* in comparison with the non-boiled control (FIG. 6). Boiling also enhanced the activity of the fraction containing molecules with molecular weight above 30 kDa (FIG. 6).

DEPOSIT INFORMATION

A deposit of the University of Arkansas Division of Agriculture proprietary *Pseudomonas fluorescens* strain designated as PBL13 disclosed above and recited in the appended claims has been made with the ARS Culture Collection (NRRL), 1815 N. University Street, Peoria, Ill. 61604. The date of deposit was Nov. 17, 2021. The deposit comprises 5 liquid nitrogen stocks, which were found viable on Nov. 18, 2021. All restrictions will be irrevocably removed upon granting of a patent, and the deposit is intended to meet all of the requirements of 37 C.F.R. §§ 1.801-1.809. The NRRL Accession Number is B-68083. The deposit will be maintained in the depository for a period of thirty years, or five years after the last request, or for the enforceable life of the patent, whichever is longer, and will be replaced as necessary during that period.

A deposit of the University of Arkansas Division of Agriculture proprietary *Burkholderia cenocepacia* strain designated as PBL18 disclosed above and recited in the appended claims has been made with the American Type Culture Collection (ATCC), 10801 University Boulevard, Manassas, Va. 20110. The date of deposit was Aug. 15, 2023. The deposit comprises 25 vials for storage at −80° C., which were found viable on Sep. 13, 2023. All restrictions will be irrevocably removed upon granting of a patent, and the deposit is intended to meet all of the requirements of 37 C.F.R. §§ 1.801-1.809. The ATCC Accession Number is PTA-127637. The deposit will be maintained in the depository for a period of thirty years, or five years after the last request, or for the enforceable life of the patent, whichever is longer, and will be replaced as necessary during that period.

We claim:

1. A method for inhibiting the growth of *Burkholderia glumae* on a rice plant comprising contacting the plant with an effective amount of a composition to inhibit the growth of *Burkholderia glumae* on the plant, wherein the composition is selected from the group consisting of: a composition comprising at least $10^8$ CFU per milliliter carrier of a *Pseudomonas* strain designated as PBL13 and deposited as NRRL Accession No. B-68083, a composition comprising at least $10^8$ CFU per milliliter carrier of a *Burkholderia cenocepacia* strain designated as PBL18 and deposited as ATCC Accession No. PTA-127637, an agricultural composition comprising a *Pseudomonas fluorescens* strain designated as PBL13 and deposited as NRRL Accession No. B-68083, an agricultural composition comprising a *Burkholderia cenocepacia* strain designated as PBL18 and deposited as ATCC Accession No. PTA-127637, and combinations thereof.

2. The method of claim 1, wherein the contacting is carried out by spraying or dusting the plant or a portion of the plant with the composition.

3. The method of claim 1, wherein the leaves of the plant are contacted with the composition.

4. The method of claim 1, wherein the contacting is carried out before flowering or during panicle formation.

5. The method of claim 1, wherein the composition comprises the *Pseudomonas* strain designated as PBL13 and deposited as NRRL Accession No. B-68083.

6. The method of claim 1, wherein the composition comprises the a *Burkholderia cenocepacia* strain designated as PBL18 and deposited as ATCC Accession No. PTA-127637.

7. A method for inhibiting the growth of *Burkholderia glumae* on a rice plant, the method comprising:

a) culturing at least one bacterial strain in a growth medium capable of supporting the growth of the bacterial strain to produce a bacterial culture composition, wherein the bacterial strain is a *Pseudomonas* strain designated as PBL13 and deposited as NRRL Accession No. B-68083, a *Burkholderia cenocepacia* strain designated as PBL18 and deposited as ATCC Accession No. PTA-127637, or a combination thereof, b) separating the bacterial strain from the bacterial culture composition to produce a cell-free composition; and c) contacting the plant with an effective amount of the cell-free composition to inhibit the growth of *Burkholderia glumae* on the plant.

8. The method of claim 7, further comprising lyophilizing the cell-free composition produced in step (b) prior to step (c).

9. The method of claim 7, wherein the at least one bacterial strain comprises the Pseudomonas strain designated as PBL13 and deposited as NRRL Accession No. B-68083.

10. The method of claim 7, wherein the at least one bacterial strain comprises the Burkholderia cenocepacia strain designated as PBL18 and deposited as ATCC Accession No. PTA-127637.

11. The method of claim 7, wherein the at least one bacterial strain comprises the Pseudomonas strain designated as PBL13 and deposited as NRRL Accession No. B-68083 and the Burkholderia cenocepacia strain designated as PBL18 and deposited as ATCC Accession No. PTA-127637.

12. The method of claim 1, wherein the composition comprises the Pseudomonas strain designated as PBL13 and deposited as NRRL Accession No. B-68083 and the Burkholderia cenocepacia strain designated as PBL18 and deposited as ATCC Accession No. PTA-127637.

* * * * *